United States Patent [19]

Strobridge

[11] Patent Number: 5,015,464

[45] Date of Patent: May 14, 1991

[54] ANTIPLAQUE CHEWING GUM

[75] Inventor: John R. Strobridge, Comstock Park, Mich.

[73] Assignee: Amway Corporation, Ada, Mich.

[21] Appl. No.: 365,741

[22] Filed: Jun. 13, 1989

Related U.S. Application Data

[63] Continuation of Ser. No. 30,175, Mar. 25, 1987, abandoned, and a continuation-in-part of Ser. No. 844,339, Mar. 26, 1986, abandoned.

[51] Int. Cl.$^5$ .................... A61K 7/16; A61K 7/26; A61K 9/68
[52] U.S. Cl. .................................. 424/48; 424/58; 426/3
[58] Field of Search ............... 424/48, 49, 58; 426/3, 426/5

[56] References Cited

U.S. PATENT DOCUMENTS

| | | | |
|---|---|---|---|
| 3,164,524 | 1/1965 | Fand et al. | 424/55 |
| 3,956,480 | 5/1976 | Dichter et al. | 424/54 |
| 4,150,151 | 4/1979 | Pader et al. | 424/49 |
| 4,252,830 | 2/1981 | Kehoe et al. | 426/5 |
| 4,291,045 | 9/1981 | Mackay et al. | 426/3 |
| 4,419,346 | 12/1983 | Stroz et al. | 424/52 |
| 4,466,954 | 8/1984 | Ichikawa et al. | 424/49 |
| 4,469,673 | 9/1984 | Iioka et al. | 424/58 |
| 4,476,107 | 10/1984 | Schmolka | 424/49 |
| 4,649,044 | 3/1987 | Gomi et al. | 424/49 |
| 4,695,463 | 9/1987 | Yang et al. | 426/3 |

OTHER PUBLICATIONS

JADA 117:515-516, Sep. 1988, ADA Council on Dental Therapeutics Accepts Listerine Gossel U.S. Pharmacist Dec. 1988, 46-51, Counseling the Consumer on Antiplaque Mouthrinses.
Gordon et al., J. Clin. Period, 12:697-704 (1985) Efficacy of Listerine Antiseptic in Inhibiting the Development of Plaque and Gingivitis.
American Pharmacy NS2Y(6):15-16, Jun. 1984, Mouth Washes May Reduce Dental Plaque, Gingivitis.
Lamster et al., Clin. Prev. Dent. 5:12-16, Nov. 1983, the Effect of Listerine ®Antiseptic on Reduction of Existing Plaque and Gingivitis.
Lusk et al., J. Am. Soc. Prefv. Vent. 4(4):31-37 (1974) Effects of an Oral Rinse on Experimental Gingivitis Plaque Formation and Formed Plaque Biosis Data Base Printout: "Listerine" (36 entries).

*Primary Examiner*—Shep K. Rose
*Attorney, Agent, or Firm*—Price, Heneveld, Cooper, DeWitt & Litton

[57] ABSTRACT

The specification discloses an antiplaque sugarfree chewing gum comprising gum base, polyol sugars, essential oils comprising antiplaque effective amounts of eucalyptol, methol, methyl salicylate and thymol, and a small amount of additional flavor oils.

46 Claims, No Drawings

ANTIPLAQUE CHEWING GUM

This application is a continuation of application Ser. No. 07/030,175 filed Mar. 25, 1987, now abandoned, itself a continuation-in-part of application Ser. No. 06/844/339, filed Mar. 26, 1986 and now abandoned.

BACKGROUND OF THE INVENTION

The present invention relates to antiplaque compositions, and especially to antiplaque chewing gums. Typically, such gums help to fight plaque by mechanically removing it from the teeth. Thus, they incorporate some type of abrasive such as zirconium silicate or the like. It is believed that the only antiplaque chewing gum commercially introduced is one which incorporates an abrasive system.

The F.D.A. categorizes chewing gum as food products. Abrasive ingredients have not been qualified as food ingredients. Hence, a gum containing such an abrasive is an adulterated food which should not be marketable except as a cosmetic or drug. Further, the long range implications of swallowing such abrasive is an unknown. Thus, the use of such abrasives in gum has to be regarded as suspect, notwithstanding the abundant showing of such gums in the patent literature.

Further, such abrasive gum products act to remove plaque only from the abraded areas, i.e., the masticating tooth surfaces. This is inadequate since plaque control is more important on the buccal, lingual and interdental surfaces.

It has long been recognized that some essential oils have some antiplaque activity. Such essential oils have been used in mouthwashes for many years.

In U.S. Pat. No. 4,170,632 issued Oct. 9, 1979 and entitled "PLAQUE INHIBITING COMPOSITIONS AND METHOD," Wagenknecht et al. teaches the use of plaque inhibiting flavor oils, specifically cinnamon, peppermint and spearmint oil in conjunction with zinc compounds in a plaque inhibiting chewing gum. U.S. Pat. No. 4,242,323 discloses a plaque inhibiting oral composition, including in one embodiment a chewing gum, comprising cocoa powder and plaque inhibiting amounts of peppermint oil, spearmint oil and/or cinnamon oil. The use of abrasives or polishing agents is also suggested.

The particular essential oils used in these two proposed gums, neither of which is believed to have been sold commercially, are flavorful and are commonly used as flavor oils. Unfortunately, they are not strongly antimicrobial and hence not exceptionally effective against plaque. The more effective antiplaque essential oils, on the other hand, do not taste very good. For example, mouthwash products incorporating the more effective antimicrobial essential oils are widely recognized to have an undesirable flavor.

Finally, many of the naturally occurring essential oils are in fact mixtures, rather than being chemically specific. Their actual composition will vary from source to source and season to season. Hence, mixture oils such as peppermint oil, spearmint oil or cinnamon oil may be more plaque effective in one season or from one source than another. This creates an unacceptable quality control problem.

SUMMARY OF THE INVENTION

We have discovered that by combining certain specific essential oils in a chewing gum, we obtain an antiplaque gum which is not only surprisingly effective against plaque, but also tastes good. Specifically, the gum must incorporate antiplaque effective amount of eucalyptol, menthol, methyl salicylate and thymol.

Other desirable aspects and features of the invention are more fully set forth in the description of the preferred embodiment.

DESCRIPTION OF THE PREFERRED EMBODIMENT

In the preferred embodiment, the product of the present invention comprises a gum base, sorbitol, mannitol, a suitable softener such as glycerine, the essential oils set forth above and a small amount of flavor oils. The preferred embodiment product has not cariogenic sugars (e.g., sucrose, glucose, fructose and dextrose) and most preferably no artificial sweeteners. Most preferably, the product contains no nonfood ingredients. A preferred formulation is as follows:

| Ingredients | Most Preferred % By Weight | Range |
| --- | --- | --- |
| Gum Base | 26% | 22-30% |
| Powdered Sorbitol | 40% | 35-45% |
| Liquid Sorbitol (70% aqueous solution) | 17% | 15-20% |
| Mannitol | 11% | 8-14% |
| Glycerine Softener | 4% | 3-5% |
| Essential Oils | 1.546% | .5-3.5% |
| Specifically: | | |
| Eucalyptol | .026% | .007-.05% |
| Menthol | 1.07% | .3-2.10% |
| Methyl Salicylate | .40% | .12-.80% |
| Thymol | .05% | .01-.10% |
| Flavor Oil Combination (spearmint, peppermint and cinnamon) | .454% | .1-.7% |

The essential oils must be present in the gum in an antiplaque effective quantity. The specific percentage required to give such and antiplaque effective quantity may vary with other ingredients in the composition, depending on what additional ingredients the skilled artisan uses. However, we have found that where the essential oils comprise from about 1.5 to about 2.5% of the gum, they are extremely effective against plaque. A wider range appears operable in at least some compositions, i.e., from about 0.5 to about 3.5%. Too little of the essential oils will render the product ineffective against plaque. Too much will render the product offensive to the taste. Indeed, too much of the essential oils may cause the product to give a burning sensation in the mouth.

The essential oils must include specifically eucalyptol, menthol, methyl salicylate and thymol. These are specific chemicals, not mixtures of chemicals as is the case with peppermint oil, spearmint oil, cinnamon oil or the like. All are recognized food grade ingredients.

Eucalyptol ($C_{10}H_{18}O$) is the active ingredient of eucalyptus oil, which is a volatile oil obtained from the fresh leaves of eucalyptus globus. It should be present in a range of from about 0.007 to about 0.05%, and preferably about 0.026%. It can be extracted from eucalyptus oil or prepared synthetically. Menthol ($CH_3C_6H_9(C_3H_7)$ OH) is a secondary alcohol obtained from peppermint oil and other mint oils, or prepared synthetically by hydrogenation of thymol. It is also known chemically as hexahydrothymol or methylhydroxyisopropyl-cyclohexane. It should be present in the gum at from about 0.3 to about 2.10%, most preferably about 1.07%.

Methyl salicylate is wintergreen oil. Its chemical formula is ($C_6H_4OHCOOCH_3$). It should be present in the gum composition in a range of from about 0.12 to about 0.80%, and most preferably about 0.40%.

Thymol, also known as thyme camphor, is methyl isopropyl phenol, $(CH_3)_2CHC_6H_3(CH_3)OH$. It is very important to the antibiotic strength of the composition and should be present in the range of from about 0.01 to about 0.10%, and most preferably 0.05%.

Typically, artisans try to keep thymol and eucalyptol out of oral products. While these ingredients are reported to have an acceptable flavor, most people find them unacceptable. However in the combination of the present invention, the overall flavor is surprisingly desirable, in spite of the presence of thymol and eucalyptol in the composition.

It is most preferably that the product also include additional flavor oils. These flavor oils may comprise spearmint, peppermint, cinnamon or most preferably a combination of all three. These additional flavor oils should be present in a range of from about 0.1 to about 0.7%, and most preferably about 0.3 to 0.5%. By incorporating these additional flavor oils, the four essential oils are rendered more palatable. While essential oil mixtures such as spearmint, peppermint and cinnamon have been said to have some antiplaque effectiveness, such effectiveness is minimal when compared to the four chemically specific essential oils discussed above. Menthol, for example, is extracted from mint oils such as peppermint and spearmint. However it is not sufficiently concentrated in the naturally occurring flavor oils to have the effectiveness desired. Hence in the present invention, the primary purpose of the peppermint, spearmint and/or cinnamon is to provide additional flavoring. Alternative flavor oils will also occur to those skilled in the art and would be acceptable in the broader aspects of the present invention.

The most preferred embodiment product of the present invention contains only food grade ingredients and is free of nonfood ingredients. Nonfood plaque inhibitors are preferably avoided. These are known plaque inhibitors which are not generally recognized as safe food ingredients. Examples includes cetyl pyridinium chloride, chlorhexidine gluconate, many zinc compounds and sanguinaria extract. Zinc compounds generally are undesirable because of their metallic or astringent taste.

Preferably, carigogenic sugars are to be avoided. These include, for example, sucrose, glucose, dextrose and fructose. In that regard, the principle sweetening ingredient relied upon in the preferred embodiment is sorbitol. The essential oils used in the present invention, at the levels used, tend to make the gum base a little sticky. Adjusting the level of sorbitol helps to offset this effect. We use from 35 to 45%, and most preferably 40% powdered sorbitol. In addition, we add between 15 and 20%, and most preferably about 17%, of a liquid sorbitol, which is a 70% aqueous solution of sorbitol. The compounder will vary the percentages of dry and liquid sorbitol with ambient process conditions.

Mannitol is also a sweetener which is used in the preferred embodiment gum. Mannitol is used as an adjunct to sorbitol for modifying the processing characteristics of the gum base. We employ from about 8 to about 14% mannitol, and most preferably about 11%.

Other polymer sugars, as for example xylitol, could also be employed in the present invention. However in the preferred embodiment, we rely on sorbitol and mannitol.

Artificial sweeteners such as sodium saccharin and sodium cyclamate, and derived sweeteners such as aspartame can be used in the broader aspects of this invention. However, it is most preferred that such sweeteners be avoided and that the polyol sugars be used. In this way, health controversies associated with the artificial and derived sweeteners are avoided.

Any conventional food grade gum base can be used in the preferred embodiment gum. Commercial gum bases are readily available. We find that the gum should comprise from about 22 to about 30% gum base, and most preferably about 26%. We incorporate an amount of glycerine, i.e., 3 to 5% and most preferably 4%, as a softener.

Experimental Results

A. Antiplaque Efficacy

To test the effectiveness of a sugarless antiplaque chewing gum made in accordance with the most preferred embodiment formula of the present invention as set forth above, 46 male/female adults, each with at least 26 natural uncapped teeth, were selected to participate in an effectiveness study. Also subjects were given a base line examination and scored using the global plaque index described in "The Clinical Quantitative Assessment of the Mechanical Cleaning Efficiency of Toothbrushes," Finkelstein, P. and Grossman, E., Clin. Prev. Dent. (b 6(3):7–12 (1984). The global plaque index measures plaque on all tooth surfaces, not just the masticating surfaces. The top 34 plaque scorers were entered into the next phase of the study after being balanced and stratified into two groups having identical global plaque scores.

After the base line determination, the 34 remaining subjects were given dental prophylaxis by a dental hygienist to remove pre-existing plaque so that effectiveness of the gum of the present invention against plaque build-up could be determined. Each was given a toothbrush and tube of commercial toothpaste and were instructed to brush in their usual manner. In addition, 17 of the subjects were given packets of the sugarless, antiplaque chewing gum made in accordance with the most preferred embodiment of this invention and instructed to chew five sticks every day. They were instructed to chew each stick of gum for 20 minutes. This chewing was to take place immediately after meals and snacks.

All of the panelists were also instructed not to use mouthwashes or mechanical cleaning aids such as floss, stimulant, oral irrigators and etc. The participants were told to return in two weeks for a second examination and in three weeks for a final examination. The results are set forth below:

|  | Mean Plaque Scores* | | |
| --- | --- | --- | --- |
|  | Baseline | Two Week | Three Week |
| Treatment Group | 18.73 | 9.826 | 7.866 |
| Number of participants | (17) | (17) | (17) |
| No Treatment Group | 18.88 | 15.876 | 13.194 |
| Number of participants | (17) | (17) | (17) |
| Reduction in Plaque | — | 38.12** | 40.33*** |

| Mean Plaque Scores* | | | |
|---|---|---|---|
| | Baseline | Two Week | Three Week |
| Build-up (%) | | | |

*Global Plaque Index Scoring Technique
**Significant at 98% Confidence Level
***Significant at 99% Confidence Level When used in accordance with these directions, the sugarless antiplaque chewing gum of this invention significantly reduced the build-up or accumulation of dental plaque. Indeed, plaque build-up was reduced substantially. There was some reduction in plaque build-up even in the group which did not get the chewing gum, merely because they were careful to follow brushing instructions. However, the additional reduction in plaque build-up achieved by chewing the gum of the present invention was striking. After two weeks, the level of plaque was 38% less for that group of 17 people who chewed the gum of the present invention. After three weeks, the level of plaque was 40% less for that group of 17 who used the gum of the present invention.

B. Flavor Attributes

The gum of the present invention was also panel tested for taste by 50 participants who chew sugarless gum daily. As above, each panelist was instructed to chew five sticks a day, one after each meal and snacks. Each stick was to be chewed for 20 minutes.

Each participant rated overall acceptability, taste/flavor and mouth freshening ability on a scale of 1 to 9, with 9 being the highest rating and 1 being the lowest. The results below show a very favorable rating in all three categories:

| | |
|---|---|
| overall acceptability | 6.43 |
| taste/flavor | 6.67 |
| mouth freshening ability | 7.18 |

The panelists were also asked to compare the gum of the present invention to their regular sugarless gum for overall acceptability, flavor lasting ability and mouth freshening ability. 34% of the panelists regularly chew Carefree TM sugarless gum, 22% Trident TM, 20% Extra TM, 2% Wrigley's TM, 2% Quench TM, 4% Bubble Yum TM, 2% Chewels TM and 10% multiple brands (4% did not indicate their regular brands). The results of this comparison are as follows:

How does the test sample compare for overall acceptability?

| | |
|---|---|
| test sample is better | 22% |
| both about the same | 42% |
| test sample is poorer | 30% |
| no answer | 6% |

How does the test samples compare for flavor lasting ability?

| | |
|---|---|
| test sample is better | 52% |
| both about the same | 24% |
| test sample is poorer | 20% |
| no answer | 4% |

How does the test sample compare for mouth freshening?

| | |
|---|---|
| test sample is better | 56% |
| both about the same | 32% |
| test sample is poorer | 8% |
| no answer | 4% |

These results show that the antiplaque gum of the present invention compares very favorably with sugarless gums generally, even though it has ingredients which are not normally considered to have a desirable flavor.

CONCLUSION

This produce obviously has striking efficacy for any consumer. The gum of the present invention provides an extremely convenient and effective means for fighting plaque. Because the gum tastes good, people enjoy chewing it. Because the flavor lasts, they chew it longer. Thus for a prolonged period of time, the plaque inhibiting essential oils of the gum are intimately contacting the teeth and fighting plaque build-up. Of course, it is understood that the above is merely a preferred embodiment of the invention and that various changes and alterations can be made without departing from the spirit and broader aspects thereof as set forth in the appended claims.

The embodiments of the invention in which an exclusive property or privilege is claimed are defined as follows.

1. An antiplaque chewing gum comprising:
   a gum base having incorporated therein and antiplaque active system consisting essentially of 0.007 to 0.05% by weight of eucalyptol, from 0.3 to 2.10% by weight of menthol, from 0.12 to 0.8% by weight of methyl salicylate and from 0.01 to 0.1% by weight of thymol, said weight percents being based on total weight of said chewing gum.

2. The antiplaque gum of claim 1 which additionally includes a small amount of additional flavor oil.

3. The antiplaque chewing gum of claim 2 which is free of cariogenic sweeteners and includes one or more noncariogenic sweeteners.

4. The antiplaque chewing gum of claim 3 which is free of nonfood plaque inhibitors, said essential oils being the principle plaque inhibitors in said gum.

5. The antiplaque chewing gum of claim 4 in which said small amount of flavor oil is selected from the group consisting of spearmint oil, peppermint oil, cinnamon oil and combinations thereof.

6. The antiplaque chewing gum of claim 5 which is free of artificial or derived sweeteners and includes a polyol sugar sweetener.

7. The antiplaque chewing gum of claim 6 in which said polyol sugar comprises sorbitol.

8. The antiplaque chewing gum of claim 7 in which said polyol sugar includes mannitol.

9. The antiplaque chewing gum of claim 8 in which said antiplaque active system comprises from about 0.5 to about 3.5% by weight of the composition.

10. The antiplaque chewing gum of claim 9 in which said antiplaque active system comprises about 1.5% by weight of said composition, based on the following amounts:

| | |
|---|---|
| eucalyptol | about .026% |
| menthol | about 1.07% |
| methyl salicylate | about .40% |

11. The antiplaque chewing gum of claim 10 in which said additional flavor oils comprise from about 0.1 to about 0.7% of said chewing gum by weight.

12. The chewing gum of claim 11 in which said additional flavor oils comprise about 0.3 to 0.5% of said chewing gum by weight.

13. The antiplaque chewing gum of claim 1 in which said antiplaque active system comprises from about 0.5 to about 3.5% by weight of the composition.

14. The antiplaque chewing gum of claim 13 which includes additional flavor oils comprising from about 0.1 to about 0.7% of said chewing gum by weight.

15. The antiplaque chewing gum of claim 14 which is free of cariogenic sweeteners and includes one or more noncariogenic sweeteners.

16. The antiplaque chewing gum of claim 15 which is free on nonfood plaque inhibitors, said essential oils being the principle plaque inhibitors in said gum.

17. The antiplaque chewing gum of claim 13 which is free of cariogenic sweeteners and includes one or more noncariogenic sweeteners.

18. The antiplaque chewing gum of claim 17 which is free of nonfood plaque inhibitors, said essential oils being the principle plaque inhibitors in said gum.

19. The antiplaque chewing gum of claim 18 which is free of artificial or derived sweeteners and includes a polyol sugar sweetener.

20. The antiplaque chewing gum of claim 19 in which said polyol sugar comprises sorbitol.

21. The antiplaque chewing gum of claim 1 in which said antiplaque active system comprises about 1.5% by weight of said composition, based on the following amounts:

| | |
|---|---|
| eucalyptol | about .026% |
| menthol | about 1.07% |
| methyl salicylate | about .40% |
| thymol | about .05%. |

22. The chewing gum of claim 21 in which said additional flavor oils comprise about 0.3 to 0.5% of said chewing gum by weight.

23. The antiplaque chewing gum of claim 1 which is free of cariogenic sweeteners and includes one or more noncariogenic sweeteners.

24. The antiplaque chewing gum of claim 23 which is free of nonfood plaque inhibitors, said essential oils being the principle plaque inhibitors in said gum.

25. The antiplaque chewing gum of claim 1 which is free of nonfood plaque inhibitors, said essential oils being the principle plaque inhibitors in said gum.

26. The antiplaque chewing gum of claim 1 which is free of cariogenic sugar, artificial or derived sweeteners and nonfood plaque inhibitors, and includes a polyol sugar sweetener.

27. The antiplaque chewing gum of claim 26 in which said polyol sugar comprises sorbitol.

28. The antiplaque chewing gum of claim 1 which is free of nonfood ingredients.

29. The antiplaque chewing gum of claim 28 which additionally includes a small amount of additional flavor oil.

30. The antiplaque chewing gum of claim 29 which is free of cariogenic sweeteners and includes one or more noncariogenic sweeteners.

31. The antiplaque chewing gum of claim 30 in which said antiplaque active system comprises from about 0.5 to about 3.5% by weight of the composition.

32. The antiplaque chewing gum of claim 31 in which said antiplaque active system comprises about 1.5% by weight of said composition, based on the following amounts:

| | |
|---|---|
| eucalyptol | about .026% |
| menthol | about 1.07% |
| methyl salicylate | about .40% |
| thymol | about .05%. |

33. The gum of claim 32 in which said additional flavor oils comprise about 0.3 to 0.5% of said chewing gum by weight.

34. The antiplaque chewing gum comprising:
from about 22 to about 30% by weight gum base and from about 0.5 to about 3.5% weight antiplaque active system consisting essentially of:

| | |
|---|---|
| eucalyptol | from about .007 to about .05% |
| menthol | from about .30 to about 2.10% |
| methyl salicylate | from about .12 to about 0.80% |
| thymol | from about .01 to about .10%. |

35. The antiplaque chewing gum of claim 34 which additionally includes from 0.1 to 0.7% additional flavor oils.

36. The antiplaque chewing gum of claim 35 which additionally includes from about 35 to about 45% powdered sorbitol; from about 15 to about 20% of a 70% aqueous solution or sorbitol; from about 8 to about 14% mannitol; and from about 3 to about 5% glycerine.

37. The antiplaque chewing gum of claim 36 in which the percentage for all of said ingredients are approximately as follows:

| Ingredients | % By Weight |
|---|---|
| Gum Base | 26% |
| Powdered Sorbitol | 40% |
| Liquid Sorbitol (70% aqueous solution) | 17% |
| Mannitol | 11% |
| Glycerine Softener | 4% |
| Eucalyptol | .026% |
| Menthol | 1.07% |
| Methyl Salicylate | .40% |
| Thymol | .05% |
| Flavor Oil Combination (spearmint, peppermint and cinnamon) | .454% |

38. The antiplaque chewing gum of claim 14 in which said antiplaque active system comprises about 1.5% by weight of said composition, based on the following amounts:

| | |
|---|---|
| eucalyptol | about .026% |
| menthol | about 1.07% |
| methyl salicylate | about .40% |
| thymol | about .05%. |

39. The chewing gum of claim 38 in which said additional flavor oils comprise about 0.3 to 0.5% of said chewing gum by weight.

40. The antiplaque chewing gum of claim 39 which is free of cariogenic sugar, artificial or derived sweeteners and nonfood antiplaque ingredients, and includes a polyol sugar sweetener.

41. The antiplaque chewing gum of claim 40 in which said polyol sugar comprises sorbitol.

42. The antiplaque chewing gum of claim 41 in which said polyol sugar includes mannitol.

43. The antiplaque chewing gum of claim 34 which is free of cariogenic sweeteners and includes one or more noncariogenic sweeteners.

44. The antiplaque chewing gum of claim 43 which is free of nonfood plaque inhibitors, said essential oils being the principle plaque inhibitors in said gum.

45. The antiplaque chewing gum of claim 44 which additionally includes from 0.1 to 0.7% additional flavor oils.

46. The antiplaque chewing gum of claim 45 which is free of nonfood ingredients.

* * * * *

UNITED STATES PATENT AND TRADEMARK OFFICE
CERTIFICATE OF CORRECTION

PATENT NO. : 5,015,464
DATED : May 14, 1991
INVENTOR(S) : John R. Strobridge, et. al.

It is certified that error appears in the above-identified patent and that said Letters Patent is hereby corrected as shown below:

On the Title page, item [75], "Inventor: John R. Strobridge, Comstock Park, Mich." should be --Inventors: John R. Strobridge, Comstock Park, Mich. and Gregory S. Evans, Grand Rapids, Mich.--

Signed and Sealed this

Twenty-fifth Day of May, 1993

Attest:

MICHAEL K. KIRK

Attesting Officer

Acting Commissioner of Patents and Trademarks